United States Patent [19]

Le Bigot et al.

[11] Patent Number: 4,562,273
[45] Date of Patent: Dec. 31, 1985

[54] PROCESS FOR PREPARING ESTERS OF FURAN BY A TRANSESTERIFICATION REACTION

[75] Inventors: Yves Le Bigot, St-Martin de Londres; Paul Audoye, Tarascon-sur-Ariege; Michel Delmas, Deyme; Antoine Gaset, Toulouse, all of France

[73] Assignee: Agrifurane, S.A., Bon Encontre, France

[21] Appl. No.: 626,112

[22] Filed: Jun. 29, 1984

[30] Foreign Application Priority Data

Jun. 29, 1983 [FR] France ............................... 83 10950

[51] Int. Cl.$^4$ ............................................ C07D 307/68
[52] U.S. Cl. ..................................... 549/473; 549/499
[58] Field of Search ................................. 549/473, 499

[56] References Cited

U.S. PATENT DOCUMENTS

| | | | |
|---|---|---|---|
| 2,433,866 | 1/1948 | Rehberg et al. ..................... | 549/499 |
| 3,996,206 | 12/1976 | Parker et al. ........................ | 536/119 |
| 4,283,414 | 8/1981 | Harney et al. ................... | 549/499 X |
| 4,291,057 | 9/1981 | Wheeler ........................... | 549/499 X |

FOREIGN PATENT DOCUMENTS 2487838 2/1982 France .

OTHER PUBLICATIONS

Ujhidy et al., Chemical Abstracts, vol. 81 (1974) 123316n.

*Primary Examiner*—Richard L. Raymond
*Attorney, Agent, or Firm*—Dutton, Jr., Harold H.

[57] ABSTRACT

A process for the preparation of an ester of furan of the formula

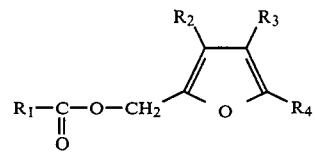

or

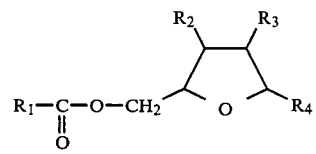

wherein $R_1$, $R_2$, $R_3$ and $R_4$ are each hydrogen or hydrocarbon radicals containing at least one heteroatom comprising subjecting an ester of the formula

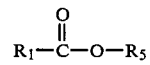

wherein $R_5$ is hydrogen or a hydrocarbon radical containing at least one heteroatom to a transesterification reaction with a furan alcohol of the formula

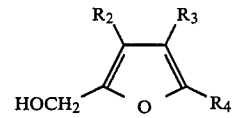

or

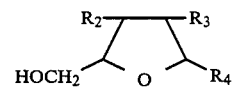

in the presence of a catalyst comprising an alkaline carbonate other than lithium carbonate at a temperature of 0° C. to 90° C.

11 Claims, No Drawings

PROCESS FOR PREPARING ESTERS OF FURAN BY A TRANSESTERIFICATION REACTION

The invention concerns a process for preparing an ester of furan by means of a transesterification reaction starting from another ester, and in particular for preparing a furfuryl ester. The invention relates to processes of the type wherein the transesterification reaction takes place in the presence of a basic transesterification catalyst consisting of an alkaline carbonate other than lithium carbonate.

BACKGROUND AND OBJECTS OF THE INVENTION

It is known that transesterification reactions are used for producing an ester which is difficult to obtain by conventional methods (synthesis), starting from another ester which however is easily prepared at moderate cost using conventional methods.

The U.S. Pat. No. 2,433,866 describes a transesterification reaction for the purpose of producing furfuryl acrylate. This reaction takes place in the presence of tertiary aluminum butylate, acting as the catalyst, and a polymerization inhibitor, and this reaction results in a mixture of ester and inhibitor which is its main drawback. The polymerization inhibitors are highly toxic products and the esters so obtained cannot be used in many fields such as foodstuffs, pharmaceuticals, cosmetics and the like. In the absence of an inhibitor, this reaction brings about spontaneous cross-linking producing polymers.

Elsewhere, U.S. Pat. No. 3,996,206, French Pat. No. 2,487,838 and other publications (in particular A. Ujhidy et al, "Method for the preparation of fatty-acid sugar esters". *Hung. J. Ind. Chem.* 1973, 4 (1), 513-32), disclose transesterification methods in the liquid/liquid phase in the presence of an alkaline carbonate, in order to obtain surfactants (the active agents in detergents). These processes are characterized by the transesterification reaction taking place at temperatures between 110° C. and 165° C., in any event higher than 110° C. These preparation procedures suffer from a major drawback in the large energy expenditure required to raise the substances to the necessary temperature. In industrial processes, very high weights of reagents (several tons) are involved and this energy consumption represents one of the primary factors burdening the cost of the new esters being produced. Also, these reactions are restricted to trans certain esters, namely triglycerides, the esters that are produced being heavy esters derived from saccharose with a highly oxygenated molecule.

There are many other esters which are very difficult and costly to produce by means of the conventional methods, but which evince exceedingly interesting properties in many industrial fields (insecticidal, analgesic, aromatic, fire-proofing properties, etc.)

The object of the present invention is to create a novel transesterification reaction which can be carried out at ambient or low temperature so as to require only a negligible expenditure in energy, or no such expense.

Another object of the invention is to provide a transesterification reaction allowing to obtain many types of esters of furan having diverse substituents. In particular the object of the invention is an especially high-performance reaction of transesterification in order to produce esters which incorporate the furan nucleus (furfuryl esters).

DESCRIPTION OF THE INVENTION

To that end, the preparation process object of the invention makes use of a transesterification reaction of an ester of formula

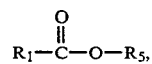

where $R_1$ and $R_5$ are hydrocarbon radicals, in the presence of a catalyst comprising an alkaline carbonate other than lithium carbonate. Within the present invention, and in order to obtain an ester of furan of the formulas

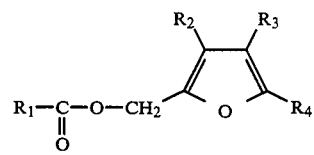

or

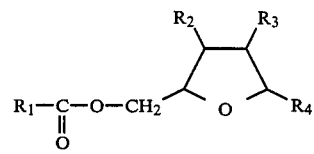

where $R_2$, $R_3$ and $R_4$ are hydrogen or hydrocarbon radicals, the transesterification reaction of the ester

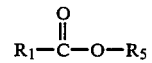

is carried out with a furan alcohol of the formula

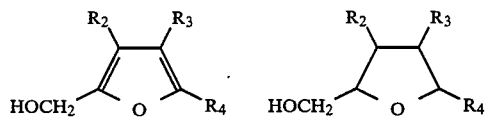

at a temperature between 0° C. and 90° C.

In particular the process of the invention allows production of furfuryl esters with known properties of flameretardancy, aromatic, bactericidal agents by using as the alcohol the furfuryl alcohol

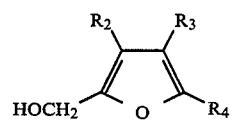

or the tetrahydrofurfuryl alcohol

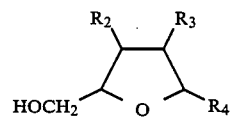

It has been unexpectedly noted that the combination of (1) a catalyst consisting of an alkaline carbonate (other than lithium carbonate), (2) a transesterification reagent comprising a furan alcohol, and (3) a moderate temperature between 0° C. and 90° C. results in a heterogeneous-phase reaction providing an excellent yield of ester, in the absence of any additional substance. The selected temperature may be room temperature and, in most instances, a temperature between 40° C. and 60° C. is preferred.

This remarkable result can be explained in the light of the novel phenomena taking place in this reaction. The transesterification takes place in the solid state and the reagents in the liquid phase (alcohol, base ester, ester product). In the prior art on the contrary when using an alkaline carbonate as the catalyst, a substantial part of the catalyst goes into the liquid phase and the transesterification essentially occurs in liquid/liquid phases, requiring a much higher input of energy. These facts explain the preconceived ideas existing in the state of the art whereby the expert was led to believe that only high temperatures would allow the transesterification reactions to take place with this kind of catalyst.

Preferably the catalyst used is potassium carbonate.

Experimentation further has shown that the transesterification reaction object of the invention can be carried out without an auxiliary solvent, the alcohol being provided in excess (over its stoichiometric proportions) and acting as the solvent. This remarkable condition in practice represents an essential advantage facilitating the industrial extraction of the obtained ester by filtering the catalyst and then distilling to eliminate the excess of alcohol, which can be recycled.

At atmospheric pressure, it is preferable to provide a great excess of alcohol corresponding to a molar ratio of furan alcohol to initial ester equal to or greater than 5. This excess displaces the reaction equilibrium and assures a good reaction yield.

It is also possible to operate at reduced pressure and in that case the excess of alcohol may be much less (molar ration between 1.5 and 3). The lowering of the pressure allows continuous extraction (by spontaneous distillation) of the formed alcohol and displaces the equilibrium toward the formation of the furan ester thereby providing a good reaction yield. In practice a pressure between 10 and 50 mm of Hg (1315 and 6575 Pascals) may be provided.

In another preferred mode of implementation of the process of the invention, the proportion of the catalyst used is between 0.05 and 0.7 moles of catalyst per mole of

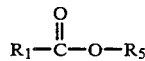

ester.

DESCRIPTION OF THE PREFERRED EMBODIMENTS

The examples below illustrate the process of the invention when implemented at atmospheric pressure (Examples 1 through 9) and when carried out at reduced pressure (Examples 10 through 15).

Operational mode for Examples 1 through 9 at atmospheric pressure

A furfuryl ester is synthesized by a transesterification reaction between an alkyl ester and furfuryl alcohol present in large excess in the presence of potassium carbonate.

Excess furfuryl alcohol, 0.02 moles of alkyl ester and a variable amount of an alkaline carbonate between 1 and 10 g are placed into a 100 ml reactor. The reaction medium is agitated at a temperature between 25° C. and 60° C. and for a time listed in Table I.

These conditions permit producing esters of furan, recovering and recycling the excess furfuryl alcohol after filtration of the solid phase. The esters of furan thereafter are obtained in pure form by means of vacuum distillation and were identified by their physical-chemical constants and by their spectroscopic characteristics (nuclear magnetic resonance of the proton and of carbon 13, infrared).

Table I below summarizes the results.

Operational mode for Examples 10 through 15 implemented at reduced pressure obtained with water vacuum pump A furfuryl ester is synthesized by transesterification reaction between an alkyl ester and furfuryl alcohol under reduced pressure obtained with a water vacuum pump (this technique, easily implemented on an industrial scale, does not demand constraining mechanical features for set-up and does not burden production costs in relation to the ambient reactions).

One mole of furfuryl alcohol and a variable amount of alkyl ester and of alkaline carbonate (Table II) are placed in a 250 ml reactor, whereupon a partial vacuum is introduced, the value of which is specified in Table II. The reaction medium is agitated and heated to a temperature as shown in Table II for three hours. The formed ethyl or methyl alcohol in the case of these selected Examples is continuously distilled during the reaction and recovered using a DEAN-STARK apparatus. At the end of the reaction, the reaction medium is distilled. The furfuryl alcohol, present in a slight excess, is recovered and recycled. Then the esters of furan are obtained in pure form by vacuum distillation and were identified by their physical-chemical constants and their spectroscopic characteristics (nuclear magnetic resonance of the proton and of carbon 13, infrared).

The results are summarized in Table II.

The above Examples were carried out using furfuryl alcohol

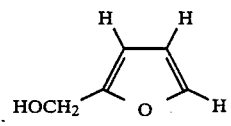

The two Examples below illustrate the use of tetrahydrofurfuryl alcohol

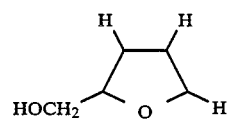

EXAMPLE 16

This Example applies to the synthesis of a furfuryl ester by means of the transesterification reaction between an alkyl ester and an excess tetrahydrofurfuryl alcohol in the presence of potassium carbonate.

0.08 moles of furfuryl alcohol, 0.02 moles of ethyl acetate and an amount of 3 g of alkaline carbonate are placed in a 100 ml reactor. The reaction medium is agitated for 3 hours at a temperature of 50° C.

These conditions make it possible to obtain an ester of furan by distillation, recovery and recycling of the excess tetrahydrofurfuryl alcohol following filtration of the solid phase, the yield being 92%. The ester of furan then is obtained in pure form by vacuum distillation and was identified by its physical-chemical constants and its spectroscopic characteristics (nuclear magnetic resonance of the proton and of carbon 13, infrared).

distillation with a yield of 95% and was identified by its physical-chemical constants and by its spectroscopic characteristics (nuclear magnetic resonance of the proton and of carbon 13, infrared).

We claim:

1. A process for the preparation of an ester of furan of the formula

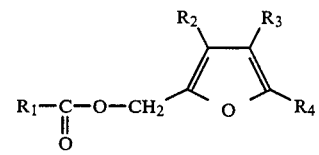

TABLE I

| Examples | Synthesized Ester of Furan | Furfuryl alcohol Initial Ester Molar Ratio | Reaction Time (Hrs) | Reaction Temperature | Nature of Catalyst and Amount in Grams | | Yield (%) |
|---|---|---|---|---|---|---|---|
| 1 | Furfuryl acetate | 5 | 8 | 60° C. | K$_2$CO$_3$ | (8 g) | 75 |
| 2 | Furfuryl acetate | 10 | 6 | 40° C. | K$_2$CO$_3$ | (3 g) | 76 |
| 3 | Furfuryl acetate | 10 | 24 | 25° C. | K$_2$CO$_3$ | (4 g) | 80 |
| 4 | Furfuryl acetate | 8 | 4 | 60° C. | Na$_2$CO$_3$ | (4 g) | 65 |
| 5 | Furfuryl acetate | 10 | 4 | 50° C. | Rb$_2$CO$_3$ | (4 g) | 80 |
| 6 | Furfuryl acetate | 10 | 4 | 50° C. | CsCO$_3$ | (4 g) | 76 |
| 7 | Furfuryl butyrate | 8 | 4 | 60° C. | K$_2$CO$_3$ | (4 g) | 78 |
| 8 | Furfuryl benzoate | 10 | 4 | 50° C. | K$_2$CO$_3$ | (4 g) | 80 |
| 9 | Furfuryl furoate | 10 | 6 | 50° C. | K$_2$CO$_3$ | (6 g) | 76 |

The reaction is totally selective. No secondary products are formed. The complement to 100 of the yield consists of the unreacted initial ester.

TABLE II

| Examples | Synthesized Ester of Furan | Furfuryl Alcohol Initial Ester Molar Ratio | Reaction Temperature | Pressure (in mm Hg) | Nature of Catalyst and Amount in Grams | | Yield (%) |
|---|---|---|---|---|---|---|---|
| 10 | Furfuryl acetate | 2 | 60° C. | 50 | K$_2$CO$_3$ | (15 g) | 90 |
| 11 | Furfuryl acetate | 1,5 | 55° C. | 30 | K$_2$CO$_3$ | (20 g) | 88 |
| 12 | Furfuryl acetate | 3 | 50° C. | 25 | Kb$_2$CO$_3$ | (10 g) | 92 |
| 13 | Furfuryl furoate | 3 | 50° C. | 20 | K$_2$CO$_3$ | (20 g) | 85 |
| 14 | Furfuryl palmitate | 3 | 60° C. | 50 | K$_2$CO$_3$ | (20 g) | 94 |
| 15 | Furfuryl stearate | 3 | 60° C. | 50 | K$_2$CO$_3$ | (20 g) | 90 |

The reaction is totally selective. No secondary product is formed. The complement to 100 of the yield consists of the unreacted initial ester.

EXAMPLE 17

This Example applies to the synthesis of a furfuryl ester by the transesterification reaction between ethyl acetate and tetrahydrofurfuryl alcohol under reduced pressure obtained using a water vacuum pump.

One mole of tetrahydrofurfuryl alcohol, 1.5 moles of ethyl acetate and 20 g of an alkaline carbonate are placed in a 250 ml reactor, and a partial vacuum of 200 mm Hg (2630 Pascals) is applied. The methyl alcohol formed in this instance is continuously distilled during the reaction and is recovered using a DEAN-STARK apparatus. Upon completion of the reaction, the reaction medium is distilled. The tetrahydrofurfuryl alcohol present in slight excess is recovered and recycled. The ester of furan then is obtained in pure form by vacuum or

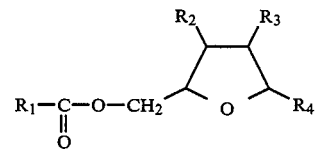

wherein R$_1$ is a hydrocarbon or furan radical, and R$_2$, R$_3$ and R$_4$ are each hydrogen or hydrocarbon radicals consisting essentially of subjecting an ester of the formula

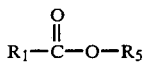

wherein R₅ is a hydrocarbon radical, to a transesterification reaction with a furan alcohol of the formula

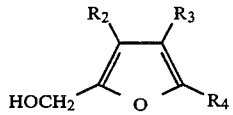

or

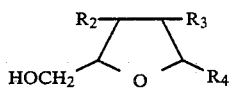

in the presence of a catalyst comprising an alkaline carbonate other than lithium carbonate at a temperature of 0° C. to 90° C.

2. A process for preparing a furfuryl ester as defined in claim 1, characterized in that the alcohol used is furfuryl alcohol wherein the radicals $R_2$, $R_3$ and $R_4$ are hydrogen.

3. A process as in claim 1 and wherein the transesterification reaction is carried out at a temperature between 40° C. and 60° C.

4. A process as in claim 3 for preparing furfuryl furoate, and wherein the transesterification reaction is based on ethyl furoate and furfuryl alcohol.

5. A process as in claim 1 and wherein potassium carbonate is used as the catalyst.

6. A process as in claim 1 and wherein the transesterification reaction is carried out in the presence of an excess alcohol acting as a solvent.

7. A process as in claim 6 and wherein the transesterification reaction is carried out at atmospheric pressure in the presence of an excess of alcohol corresponding to a molar ratio of furan-alcohol/initial-ester equal to or greater than 5.

8. A process as in claim 6, and wherein the transesterification reaction is carried out at a pressure between 10 and 50 mm Hg (i.e. between 1315 pascals and 6575 pascals) in the presence of a slight excess of alcohol corresponding to a molar ratio of furan-alcohol/initial-ester between 1.5 and 3.

9. A process as in claim 1 and wherein the proportion of catalyst is between 0.05 and 0.7 moles of catalyst per mole of

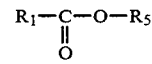

ester.

10. A process for the preparation of esters of furan of the formula

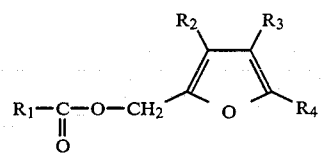

or

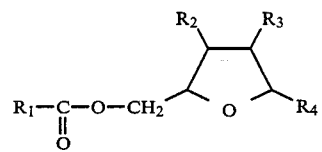

wherein $R_1$ is a hydrocarbon or furan group and $R_2$, $R_3$ and $R_4$ are hydrogen or hydrocarbon radicals, the process consisting essentially of subjecting an ester of the formula

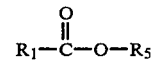

wherein $R_5$ is methyl or ethyl to a transesterification reaction with furfuryl alcohol or tetrahydrofurfuryl alcohol in the presence of a catalyst comprising an alkaline carbonate other than lithium carbonate at a temperature of 0° C. to 90° C.

11. A process as in claim 10 and wherein said ester is selected from the group consisting of acetate, butyrate, benzoate, furoate, palmitate or stearate esters.

* * * * *